(12) United States Patent
Sangiovani

(10) Patent No.: US 7,731,773 B2
(45) Date of Patent: Jun. 8, 2010

(54) IMPACT DIESEL PARTICULATE FILTER

(75) Inventor: Sergio Varkala Sangiovani, Santana (BR)

(73) Assignee: Sabertec, L.L.C., Austin, TX (US)

( * ) Notice: Subject to any disclaimer, the term of this patent is extended or adjusted under 35 U.S.C. 154(b) by 283 days.

(21) Appl. No.: 11/743,911

(22) Filed: May 3, 2007

(65) Prior Publication Data

US 2008/0066446 A1    Mar. 20, 2008

Related U.S. Application Data

(60) Provisional application No. 60/746,341, filed on May 3, 2006.

(51) Int. Cl.
*B01D 46/24* (2006.01)
*F01N 3/022* (2006.01)

(52) U.S. Cl. ............................. 55/482; 55/484; 55/525; 55/DIG. 30; 60/311

(58) Field of Classification Search ............... 55/385.3, 55/482, 484, DIG. 30, 485, 486, 487, 488, 55/489, 525; 60/295, 303, 311
See application file for complete search history.

(56) References Cited

U.S. PATENT DOCUMENTS

| | | | | |
|---|---|---|---|---|
| 3,871,850 A | * | 3/1975 | Lenane | 55/486 |
| 3,954,618 A | * | 5/1976 | Strauss | 210/232 |
| 4,297,116 A | * | 10/1981 | Cusick | 55/319 |
| 4,469,079 A | | 9/1984 | Cook | |
| 4,478,618 A | * | 10/1984 | Bly et al. | 55/314 |
| 4,576,799 A | * | 3/1986 | Worner et al. | 422/176 |
| 5,138,836 A | * | 8/1992 | Pfister | 60/311 |
| 5,205,850 A | * | 4/1993 | Jenrich et al. | 55/350.1 |
| 5,238,472 A | * | 8/1993 | Pfister et al. | 55/282.3 |
| 5,246,472 A | * | 9/1993 | Herman et al. | 96/380 |
| 5,248,481 A | | 9/1993 | Bloom et al. | |
| 5,248,482 A | * | 9/1993 | Bloom | 422/174 |
| 5,258,164 A | * | 11/1993 | Bloom et al. | 422/174 |
| 5,293,742 A | * | 3/1994 | Gillingham et al. | 60/288 |
| 5,376,341 A | * | 12/1994 | Gulati | 422/179 |
| 5,830,250 A | * | 11/1998 | Shirk et al. | 55/498 |

(Continued)

OTHER PUBLICATIONS

International Search Report; International Application No. PCT/US07/68132; dated Dec. 4, 2007.

*Primary Examiner*—Michael A Marcheschi
*Assistant Examiner*—Robert A Clemente
(74) *Attorney, Agent, or Firm*—DuBois, Bryant & Campbell, LLP; William D. Wiese

(57) ABSTRACT

An emission reduction device which may be removably affixed to a diesel engine's exhaust system. The device comprises an outer casing which may be divided into a lower portion and an upper portion, the lower portion of which is removably attachable to the exhaust system of a diesel engine; a carcass for holding a bobbin wherein the carcass is attached to the lower portion of the outer casing at the point where the exhaust enters the outer casing and the carcass has a beveled opening in a diagonal line in its proximal part and a bobbin positioned in its distal part; one or more fibrous blanket cylinders; and a guide for arranging and securing the one or more fibrous blanket cylinders within the outer casing. The fibrous blanket cylinders may be wrapped in a wire mesh. In an alternative embodiment, a second fibrous blanket formed into a cone with the larger diameter of the cone positioned proximally may be removably inserted in the carcass.

5 Claims, 10 Drawing Sheets

U.S. PATENT DOCUMENTS 6,013,118 A * 1/2000 Matsunuma et al. ....... 55/282.3
6,767,378 B2 * 7/2004 Nishiyama et al. ............ 55/309
6,835,224 B2 * 12/2004 Cheng ......................... 55/428
7,452,831 B2 * 11/2008 Yamada et al. .............. 442/239
2004/0128964 A1 * 7/2004 Cheng ......................... 55/428
2005/0109023 A1 5/2005 Kudo et al.

* cited by examiner

IMPACT DIESEL PARTICULATE FILTER

CROSS-REFERENCE TO RELATED APPLICATION

This non-provisional application claims priority based upon prior U.S. Provisional Patent Application Ser. No. 60/746,341 filed May 3, 2006 in the name of Sergio Varkala Sangiovani, entitled "System and Method for Reduction of Emissions," the disclosure of which is incorporated herein by reference.

BACKGROUND OF THE INVENTION

There is a need for a method and system capable of efficiently and effectively filtering pollutants from exhaust gases. Although there are a number of devices available which are useful for filtering exhaust gases from diesel engines, each of these devices is incapable of providing an effective method for reducing pollutants cost effectively for the reasons described herein.

In a diesel engine, air is drawn into the cylinders and is compressed by the pistons at compression ratios as high as 25:1, much higher than used for spark-ignited combustion engines. Near the end of the compression stroke, diesel fuel is injected into the combustion chamber through an injector (or atomizer). The fuel ignites from contact with the air that due to compression has been heated to a temperature of about 700-900° C. The resulting combustion causes increased heat and expansion in the cylinder which increases pressure and moves the piston downward. A connecting rod transmits this motion to a crankshaft to convert linear motion to rotary motion for use as power in a variety of applications. Intake air to the engine is usually controlled by mechanical valves in the cylinder head. For increased power output, most modern diesel engines are equipped with a turbocharger, and in some derivatives, a supercharger to increase intake air volume. Use of an aftercooler to cool intake air that has been compressed, and thus heated, by the turbocharger increases the density of the air and typically leads to power and efficiency improvements.

In general, diesel emissions are bi-products of diesel combustion. This can be a function of injection within the engine. For example, advancing the start of injection (injecting before the piston reaches top of dead center) results in higher in-cylinder pressure and temperature, and higher efficiency, but also results in higher emissions of oxides of nitrogen oxides through higher combustion temperatures. At the other extreme, delayed start of injection causes incomplete combustion and emits visible black smoke made of particulate matter and unburned hydrocarbon. While many diesel emissions are problematic, the most highly regulated diesel emissions are:

1. Diesel Particuiate Material ("PM", or "DPM") (also referred to as "Diesel Particulate Matter", "Particulate Material", or "Particulate Matter"): Particulate matter is an aerosol comprised of complex physical and chemical structures. Particulate matter contributes to the greenhouse effect, it causes grave environmental damage, and it seriously affects human health. Particulate matter is primarily responsible for the black smoke normally associated with diesel exhaust. It is also a primary source of urban smog.
2. Nitrogen Oxides ($NO_x$): Nitrogen Oxides are highly active ozone precursors and account for a large component of visible smog. Besides particulate matter, nitrogen oxides are one of the most pollutive diesel emissions.
3. Hydrocarbons (HC): The production of hydrocarbons is often a result of the inefficient combustion of fuel and engine lube oils. In the atmosphere, hydrocarbons undergo photochemical reactions with nitrogen oxides leading to formation of smog and ground level ozone.
4. Carbon Monoxide (CO): This is a highly toxic greenhouse gas that is poisonous to humans and is a contributor to global warming.

Examples of non-regulated bi-products of diesel combustion include polynuclear aromatic hydrocarbons, aldehydes, sulfur dioxide, nitrous oxide, and metal oxide.

Inefficient combustion of diesel fuel produces emissions that pollute the environment and harm human health. The environmental consequences of particulate material emissions include air pollution, water pollution, acid rain, acidification of waterways, deforestation, smog, reduced atmospheric visibility, crop degradation, global warming, and climate forcing. In addition, the human health consequences of particulate material emissions include cardiovascular disease, respiratory disease, cancer, fibrosis, allergic responses, reduced pulmonary function, worsening of asthmatic symptoms and occurrences, increased morbidity, and premature death. Moreover, a number of internationally publicized studies demonstrate a high correlation between ambient particulate material and increases in adverse health outcomes such as respiratory hospital admissions, emergency room visits, restricted activity days, respiratory symptoms for adults, lower respiratory tract illnesses for children, asthmatic attacks, chronic diseases, and mortality.

Although conventional diesel emission filtration technologies are numerous, there are essentially two categories into which all such technologies fall:

1. Catalyzed Diesel Particulate Filters ("CDPFs"): catalyzed diesel particulate filters are referred to by many different names. Some of the most commonly used—and misused—are: "catalytic converters," "catalytic Reactors," "catalytic purifiers," "exhaust purifiers," "trap filters," "diesel traps," "exhaust scrubbers," "catalyst filters," "catalyzed wall-flow filters," "wall-flow filters," and "catalytic mufflers."
2. Diesel Oxidation Catalysts ("DOCs"): diesel oxidation catalysts are also commonly referred to as "oxidation catalysts," "flow-through catalysts," and "flow-through devices."

Both catalyzed diesel particulate filters and diesel oxidation catalysts employ the same basic method to achieve the reduction of particulate materials; they utilize heat to "oxidize" or bun the particulate material. In most cases, the heat from the engine's exhaust system is used to achieve oxidation. The reoccurring process of oxidation is also often referred to "regeneration" because the process of oxidation not only reduces particulate material emissions, it also regenerates the catalytic device's filtration capacity.

In order for the process of regenerative oxidation to occur, high temperatures, normally between 250° and 350° C., must be attained and preferably sustained during operation. In many operating conditions, attaining sufficiently high temperatures can prove difficult or unattainable. Catalytic devices (CDPF's and DOC's) employ precious metals such as platinum, palladium and rhodium as catalysts to lower the minimum temperatures necessary to achieve "light off", the point at which oxidation of the particulate material is initiated. Manufactures use these highly conductive, and very expensive, metals to coat or impregnate the substrate surfaces of their catalytic devices.

The catalytic devices discussed above can generally be described as either active or passive. Catalytic technologies which rely on heat from an engine's exhaust system in order to achieve oxidation are frequently referred to as "passive" catalytic devises. Other systems may incorporate fuel burners, electric heating elements, and fuel-borne additives which aid in attaining the temperatures at which oxidation occurs. Technologies which employ these types of components are often referred to as "active" catalytic devices.

For purposes of eliminating potential confusion, it should be noted that some manufacturers define catalyzed diesel particulate filters which only contain precious metal catalysts as "active" devices, even though these devices rely solely upon the heat contained in an engine's exhaust to achieve oxidation. This classification usually occurs when the manufacturer also produces a diesel particulate filter which contains no catalyst, i.e. a device which is in all other ways similar to a catalyzed diesel particulate filter, however; the device relies solely upon the heating of its component base metal to achieve temperatures sufficient to initiate oxidation. Because exhaust temperatures are commonly required to exceed 500° C. for these non-catalyzed devices to affect oxidation, their widespread use is significantly restricted.

The primary difference between catalyzed diesel particulate filters and diesel oxidation catalyst technologies is that catalyzed diesel particulate filter technologies physically trap and store particulate material—usually by using catalyzed ceramic, cordierite or silicon carbide wall flow monoliths, or ceramic fiber or ceramic cartridge filters. Once the particulate material becomes trapped, it is oxidized and particulate material emissions are reduced.

Conversely, diesel oxidation catalyst technologies do not trap particulate material emissions. Rather, particulate materials "pass-through" the internal structures of these devices. When exhaust gases traverse the catalyst, carbon monoxide, gaseous hydrocarbons and liquid hydrocarbon particles are oxidized, thereby reducing total particulate material emissions.

There are a number of other differences between catalyzed diesel particulate filters and diesel oxidation catalyst technologies as well. For example, catalyzed diesel particulate filters can achieve particulate material filtration rates of ≧90% given specific, controlled operating conditions. Moreover, catalyzed diesel particulate filters reduce each sub-category of particulate material (i.e. solid inorganic fractions, solid organic fraction and sulfate particulates). It is necessary to note however, the application and effectiveness of catalyzed diesel particulate filters technology is significantly constrained by the following limitations:

- Catalyzed diesel particulate filters are very expensive. The California Air Resources Board provides cost-range information for DPF's corresponding to the following engine capacitates:
  - 100 horsepower: US$5,000-US$7,000
  - 275 horsepower: US$6,900-US$9,000
  - 400 horsepower: US$10,000 average
  - 1,400 horsepower: US$32,000+
- Catalyzed diesel particulate filters are incapable of affecting particulate material emissions reductions when using fuels that exceed 150 ppm Sulfur.
- Catalyzed diesel particulate filters performance is adversely affected by insufficient operating temperatures.
- In less-than-optimal conditions, catalyzed diesel particulate filters are prone to clogging and failure. When failure occurs, the potential for engine damage or destruction is significant.
- Because catalyzed diesel particulate filters can create significant engine back pressure, expensive engine recalibrations are often required upon their installation.
- catalyzed diesel particulate filters often need to be equipped with expensive electronic back pressure monitoring devices, such as data loggers.
- Because passive catalyzed diesel particulate filters regeneration is entirely dependent on operating temperature, passive catalyzed diesel particulate filters do not work under "low load" conditions.
- "Active" components in catalyzed diesel particulate filter technologies significantly increase catalyzed diesel particulate filters unit price and complexity.
- Catalyzed diesel particulate filters do not work well on older engines.
- Catalyzed diesel particulate filters can become a source of hazardous zinc, sulfuric, calcium, and phosphorus ash particulate.
- Catalyzed diesel particulate filters can reduce engine performance.
- Catalyzed diesel particulate filters often produce fuel economy penalties.

According to the United States Department of Energy (US-DOE), fuel sulfur has significant effects on post-filter total particulate material emissions, and, as fuel sulfur levels increase, catalyzed diesel particulate filter reduction efficiencies decreases to a point where they actually becomes a source of particulate emissions when using fuels with sulfur concentrations ≧150 PPM.

Tests conducted by the USDOE report that catalyzed diesel particulate filters that achieved 95% reductions of particulate material emissions when using fuels with 3 ppm sulfur concentrations had their filtration efficiencies reduced to only 74% when using fuels with 30 ppm sulfur concentrations. Further, these same devices were reduced to particulate material filtration rates of 0% to −3% when using fuels with 150 ppm sulfur concentrations, and they experienced total particulate material emissions increases of 122% to 155% when using fuels with sulfur concentrations ≧350 ppm.

Moreover, the Natural Resources Defense Council (NRDC) has stated that catalytic technologies can not work properly if there is sulfur in the fuel—and in some cases, sulfur in the fuel will render the catalytic filtration equipment and even the vehicle inoperable.

By comparison, diesel oxidation catalyst technologies are generally less expensive than catalyzed diesel particulate filter technologies, and because diesel oxidation catalysts are "flow through", instead of "wall flow" devises, they do not have the same propensity to create engine back pressure, clog and/or cause potential engine damage like their catalyzed diesel particulate filter counterparts. Diesel oxidation catalysts can achieve particulate material filtration rates between 19% and 50%. However, the application of diesel oxidation catalyst technology is constrained by the following:

- Diesel oxidation catalysts are too expensive for widespread application. The California Air Resources Board provides cost average information for diesel oxidation catalysts corresponding to the following engine capacitates:
  - 275 horsepower: US$2,100
  - 400 horsepower: US$20,000+
  - The Everett School District in Washington state reported an average per-unit-cost of US$2,500 per DOC for each bus in its fleet
- Diesel oxidation catalyst reduction of total particulate material is significantly reduced when using fuels with high sulfur fuels.

Diesel oxidation catalysts do not filter solid organic fraction sometimes called "dry") particulate and dry particulates typically comprise the majority of total particulate material.

Diesel oxidation catalysts do not work well on older engines.

Diesel oxidation catalyst effectiveness is extremely dependent upon operating temperatures.

When operating at higher temperatures, diesel oxidation catalysts oxidize sulfur oxides, and in doing so become generators of sulfuric acid. When this occurs, diesel oxidation catalysts create a net increase total particulate material emissions by increasing production of sulfate particulates at rates that offset soluble organic fraction reductions The University of Washington's Extension Energy Program has stated that diesel oxidation catalysts can oxidize sulfur dioxide to form sulfate particulates (sulfuric acid ($H_2SO_4$)). Therefore, high sulfur content fuels can increase total particulate emissions via the production of sulfuric acid, which can offset soluble organic fraction (sometimes called "wet" particulate material) reductions."

The United States Department of Energy has found statistically significant increases in particulate material with high sulfur fuel due almost exclusively to the increase in the $SO_4$ fraction of the total particulate material. At this high exhaust temperature (405° C. at catalyst inlet), the diesel oxidation catalyst accelerates the conversion of $SO_2$ to $SO_3$, thereby increasing the $SO_4$ fraction of the particulate material. As expected, the effect is seen only with the higher sulfur (150 ppm and 350 ppm sulfur content) fuels. With the 350 ppm sulfur content fuel, post catalyst particulate material emissions were approximately 200% higher than those measured without an active catalyst.

Despite the promoted efficiency of the methods and systems of the prior art, many are impracticable from the commercial point of view for the reasons set forth above. Moreover, the use of fuel with low concentration of sulphur (below 130 ppm) is an essential factor in the employment of catalytic regeneration filters. In Brazil and in the majority of the countries, the diesel is sold with 2000 ppm of sulphur. Therefore using the catalytic regeneration filters in diesel that contains more than 300 ppm of sulphur, turn the filters into a source of pollution.

SUMMARY OF THE INVENTION

The system and method described herein relate to a novel solution for the improved use of fuel and the treatment of gases emitted from diesel engines and, more specifically, the gases that are emitted through exhaust pipes of vehicles such as automobile vehicles and industrial equipment. An objective of the present invention is to reduce environmental pollution and, as a result, to improve the conditions of life, including the quality and quantity of the flora and fauna on the planet Earth. The emission of pollutant gases in the atmosphere has significantly contributed to contamination of the environment. There is an overwhelming demand for a solution capable of curbing the alarming effects caused by worldwide environmental degradation.

The present invention provides a variety of ecologic and economic advantages. For example, because the present invention filters particulates and greatly reduces the amount of carbon monoxide, hydrocarbons and other gases produced by the combustion of fuel, this invention has direct effect in the improvement of the environment. This minimizes the damaging effects of the environmental phenomenon known as the "greenhouse effect" and improves the air quality in urban centers.

In one embodiment, the present invention comprises an outer casing which may be divided into a lower portion and an upper portion, the lower portion of which is removably attachable to the exhaust system of a diesel engine; a carcass for holding a bobbin wherein the carcass is attached to the lower portion of the outer casing at the point where the exhaust enters the outer casing and the carcass has a beveled opening in a diagonal line in its proximal part and a bobbin positioned in its distal part; one or more fibrous blanket cylinders; and a guide for arranging and securing the one or more fibrous blanket cylinders within the outer casing. The fibrous blanket cylinders may be wrapped in a wire mesh. In an alternative embodiment, a second fibrous blanket formed into a cone with the larger diameter of the cone positioned proximally may be removably inserted in the carcass.

Results from initial tests of one embodiment of the present invention show that the device filters up to 69% of total particulate matter at a cost that is significantly less than either catalyzed diesel particulate filters or diesel oxidation catalysts. Moreover, the device is extremely effective with high sulfur content fuels (i.e. greater than 500 ppm sulfur). The device performs effectively on older engines, does not create engine back pressure, does not reduce engine fuel economy, captures both wet and dry particulate matter, is extremely durable, is easy to install and maintain, lasts indefinitely, and does not produce hazardous sulfur, lead or zinc bi-products. In addition, the device is effective under both high and low load conditions and its efficacy is not affected by engine operating temperatures.

In addition, the invention also reduces the level of noises emitted from the exhaust system by acting as a sound baffle, thereby reducing noise pollution.

For all these reasons, and many others, the device and method of the present invention represents an innovation in the field of emission control.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE EMBODIMENTS

The present invention provides an efficient device and method for reducing the emission of harmful gases in the environment, reducing noise, reducing the consumption of fuel, and improving an engine's performance, all in a cost effective manner. The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

In one embodiment, the present invention comprises an outer casing which may be divided into a lower portion and an upper portion, the lower portion of which is removably attachable to the exhaust system of a diesel engine; a carcass for holding a bobbin wherein the carcass is attached to the lower portion of the outer casing at the point where the exhaust enters the outer casing and the carcass has a beveled opening in a diagonal line in its proximal part and a bobbin positioned in its distal part; one or more fibrous blanket cylinders; and a guide for arranging and securing the one or more fibrous blanket cylinders within the outer casing. The fibrous blanket cylinders may be wrapped in a wire mesh. In an alternative embodiment, a second fibrous blanket formed into a cone with the larger diameter of the cone positioned proximally may be removably inserted in the carcass.

Figure 1:
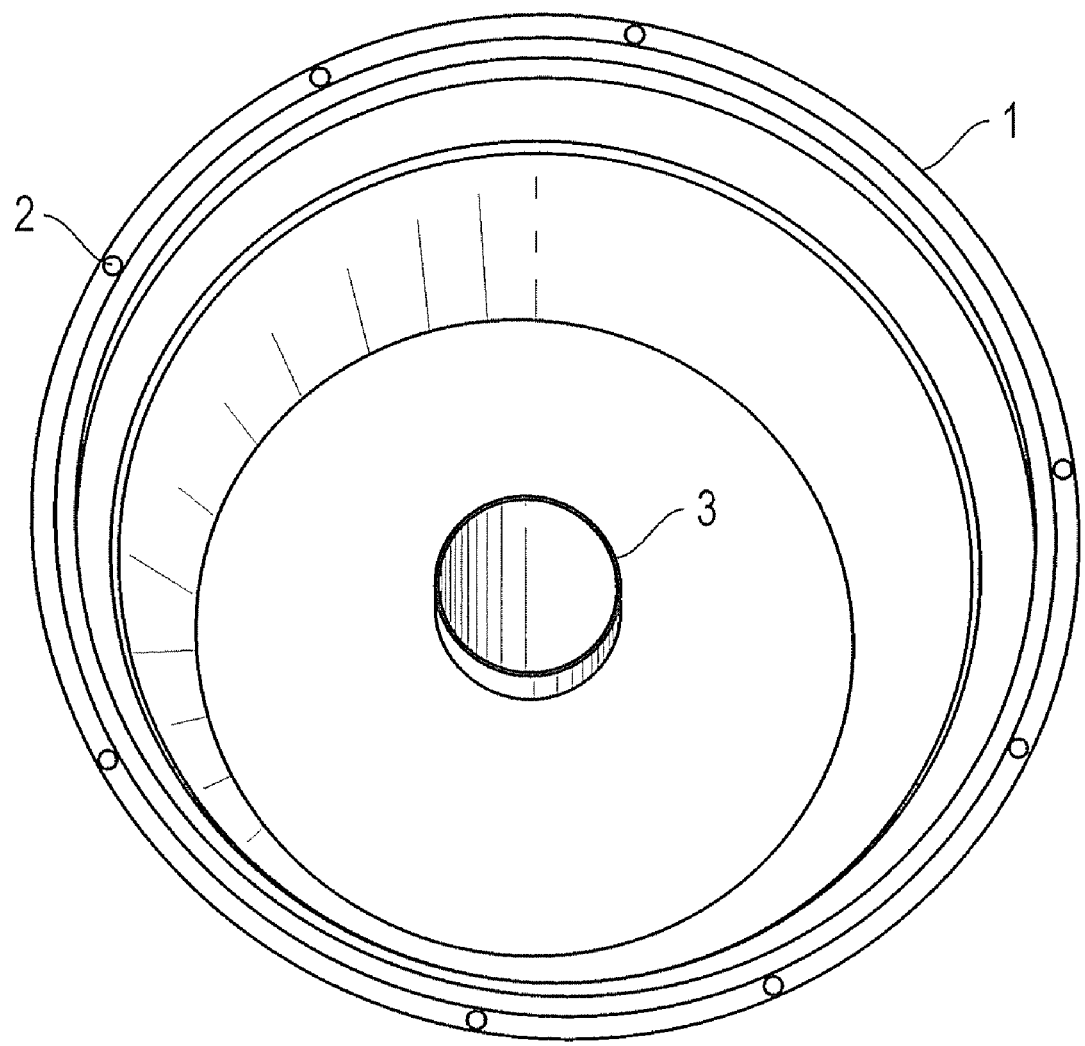
FIG. 1 shows a top view of the lower portion of the outer casing of one embodiment of the device of the present invention.

Referring now to the drawings, FIG. 1 shows one embodiment of the lower portion of the outer casing 1 wherein an exhaust inlet 3 is positioned in the proximal end thereof. The proximal end of the exhaust inlet 3 may be affixed to the exhaust system of a diesel engine and the distal end of the exhaust inlet is affixed to, and forms an integral part of, the lower portion of the outer casing 1. The exhaust inlet 3 may be attached to the exhaust system in a variety of ways using a variety of attachment devices known in the art. The exhaust inlet 3 may be either permanently or removably attached to the exhaust system. The lower portion of the outer casing 1 may be made of any material capable of withstanding the heat and pressure of the application, such as for example, steel, aluminum, aluminized steel or stainless steel.

Figure 2:
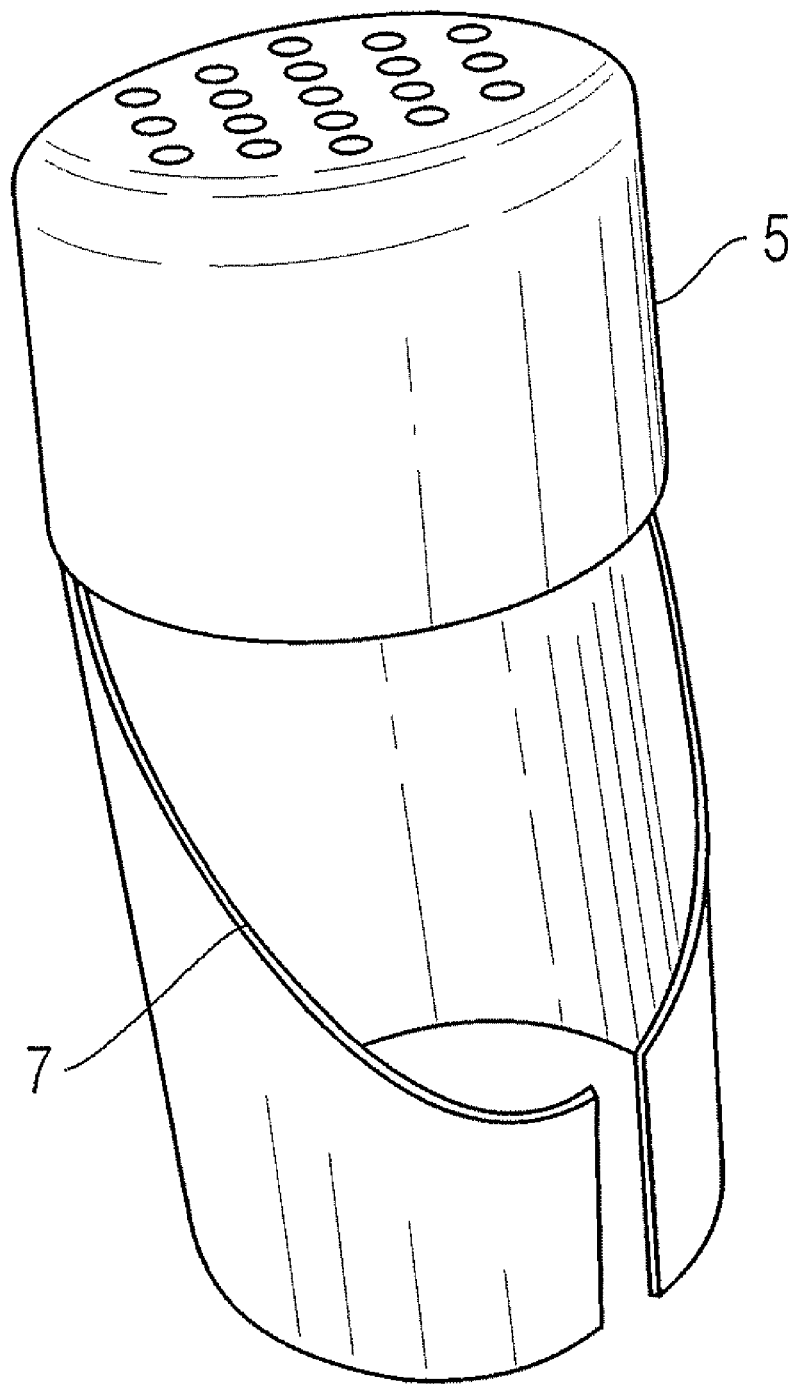
FIG. 2 shows a side view of the carcass of one embodiment of the device.

FIG. 2 shows a side view of one embodiment of the carcass 5. The carcass 5 is generally cylindrical with a beveled opening 7 in a diagonal line in its proximal part where it is affixed to the distal end of the exhaust inlet. The distal end of the carcass 5 is configured for the passage of air, either through the placement of a screen or mesh at the end thereof, or by perforating the material used to construct the carcass 5. The distal end of the carcass 5 is also adapted to receive and to fix a bobbin 9. The carcass 1 may be made of any material capable of withstanding the heat and pressure of the application, such as for example, steel, aluminum, aluminized steel or stainless steel. The screen may be metallic such as, for example, a punched metal web or a wire mesh. The bobbin 9 may be made of one or more metals or of other materials capable of withstanding the heat and pressure of an exhaust system and may be constructed by wrapping two metal fabrics around a central point. The carcass 5 may be attached to the exhaust inlet 3 in a variety of ways using a variety of attachment devices known in the art. The carcass 5 may be either permanently or removably attached to the exhaust inlet 3.

In an alternative embodiment, a diaphragm formed by wrapping a fibrous blanket into a cone with the larger radius positioned proximally and the smaller radius positioned distally may be removably inserted in the carcass 5. In one embodiment of the invention, the diaphragm is constructed in such a manner that the overlapping ends at the narrow end of the cone are secured together and, in another configuration, the overlapping ends at the narrow end of the cone are allowed to overlap but are not secured to one another. The diaphragm may be removably attached to the carcass 5. The diaphragm may be made of any material capable of filtering particulate materials including one or more of an aramid, a meta-ararmid, a polyamide, a polyphenylene sulfide, a p-phenylene-1,3,4-oxadiazole, polytetrafluoroethylene, and basalt.

Figure 3:
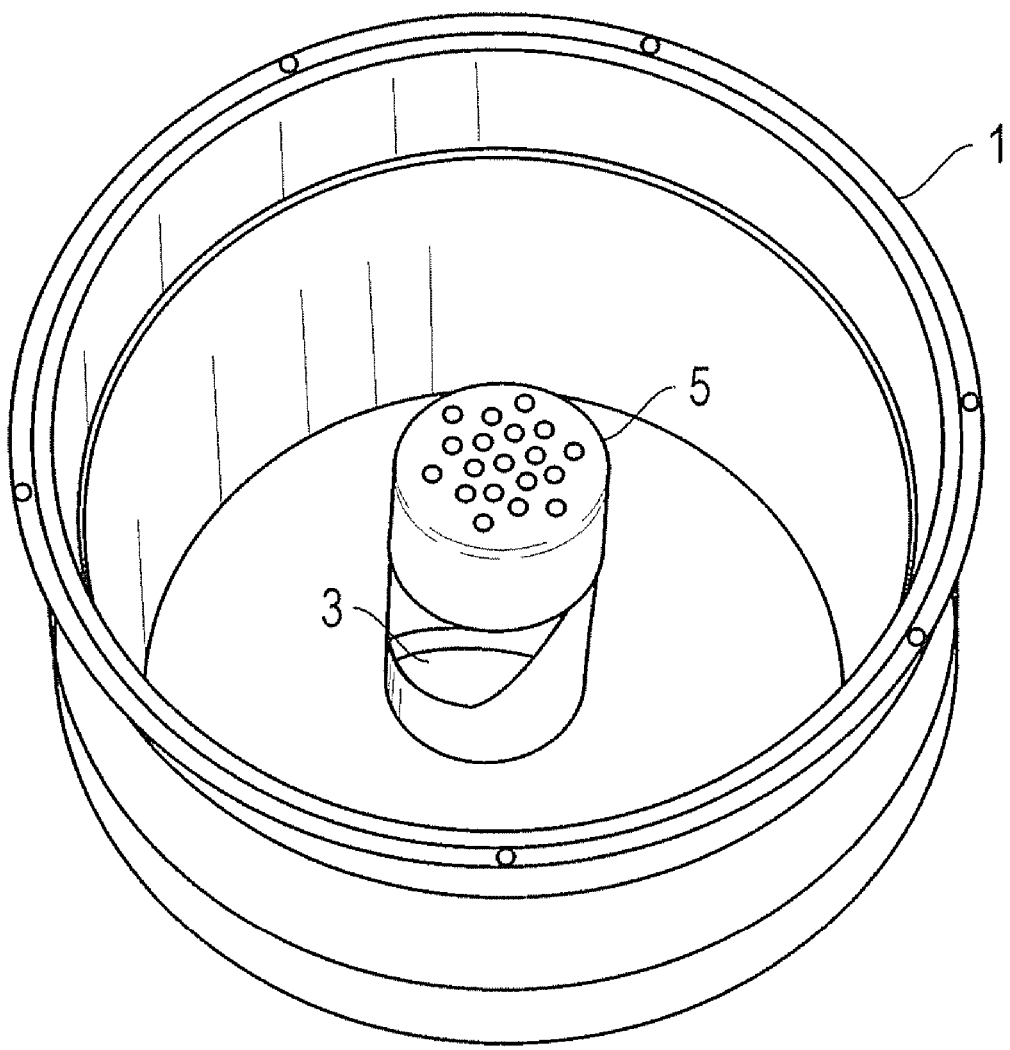
FIG. 3 shows the carcass installed in the lower portion of the outer casing in one embodiment of the device of the present invention.

FIG. 3 shows the carcass 5 attached to the distal end of the exhaust inlet 3. The bobbin 9 is visible through the perforations in the distal end of the carcass 5.

Figure 4:
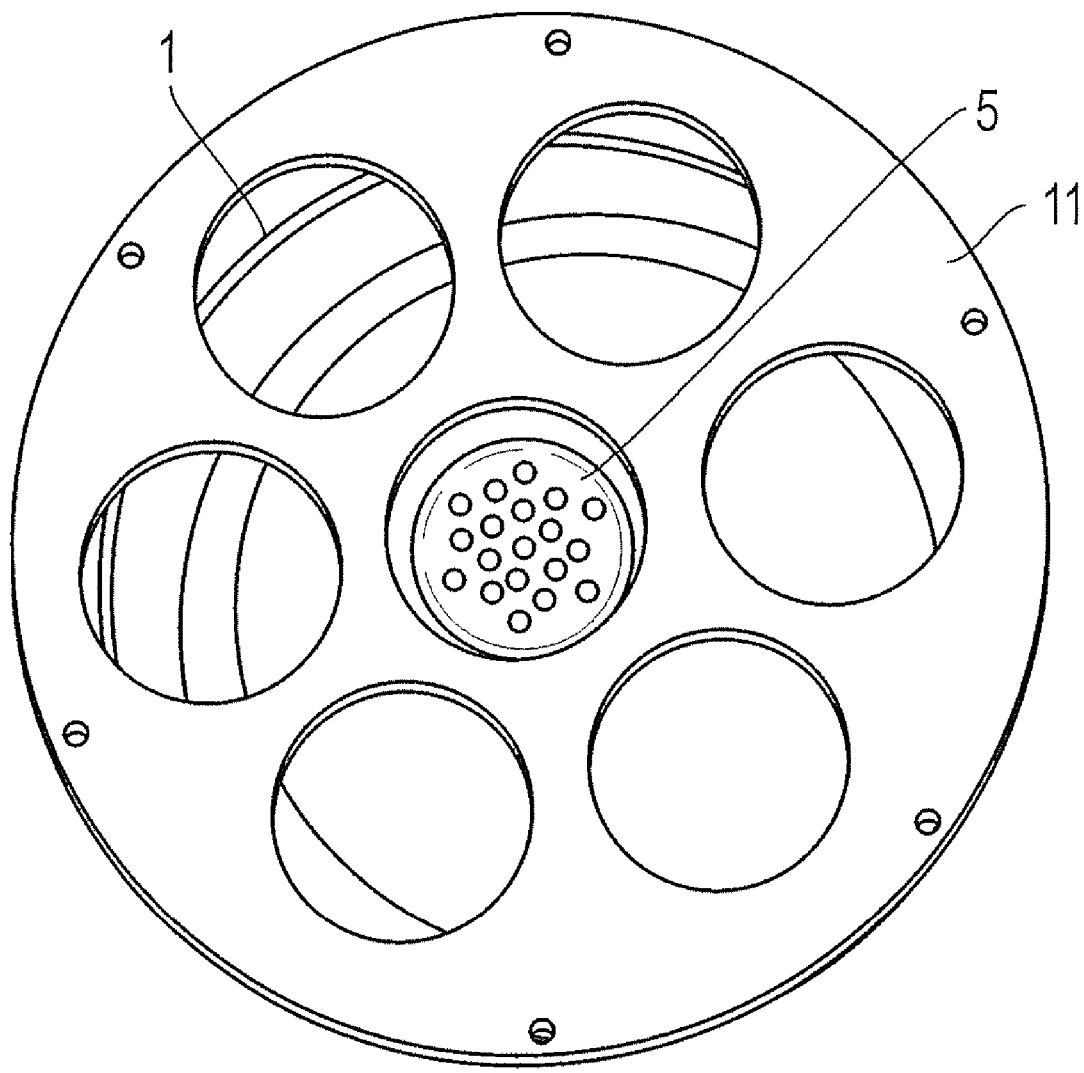
FIG. 4 shows a perspective view of the guide for the fibrous blanket cylinders.

FIG. 4 shows one embodiment of a guide 11 for arranging and securing fibrous blanket cylinders 13 within the outer casing. In the configuration shown, the guide is configured for the placement of seven cylinders however more or fewer cylinders may be used as desired. As shown, the distal end of the carcass 5 is visible through the center hole in the guide 11 although that configuration is not essential to the operation of the device. The guide 11 may be made of any material capable of withstanding the heat and pressure of the application, such as for example, steel, aluminum, aluminized steel or stainless steel.

Figure 5:
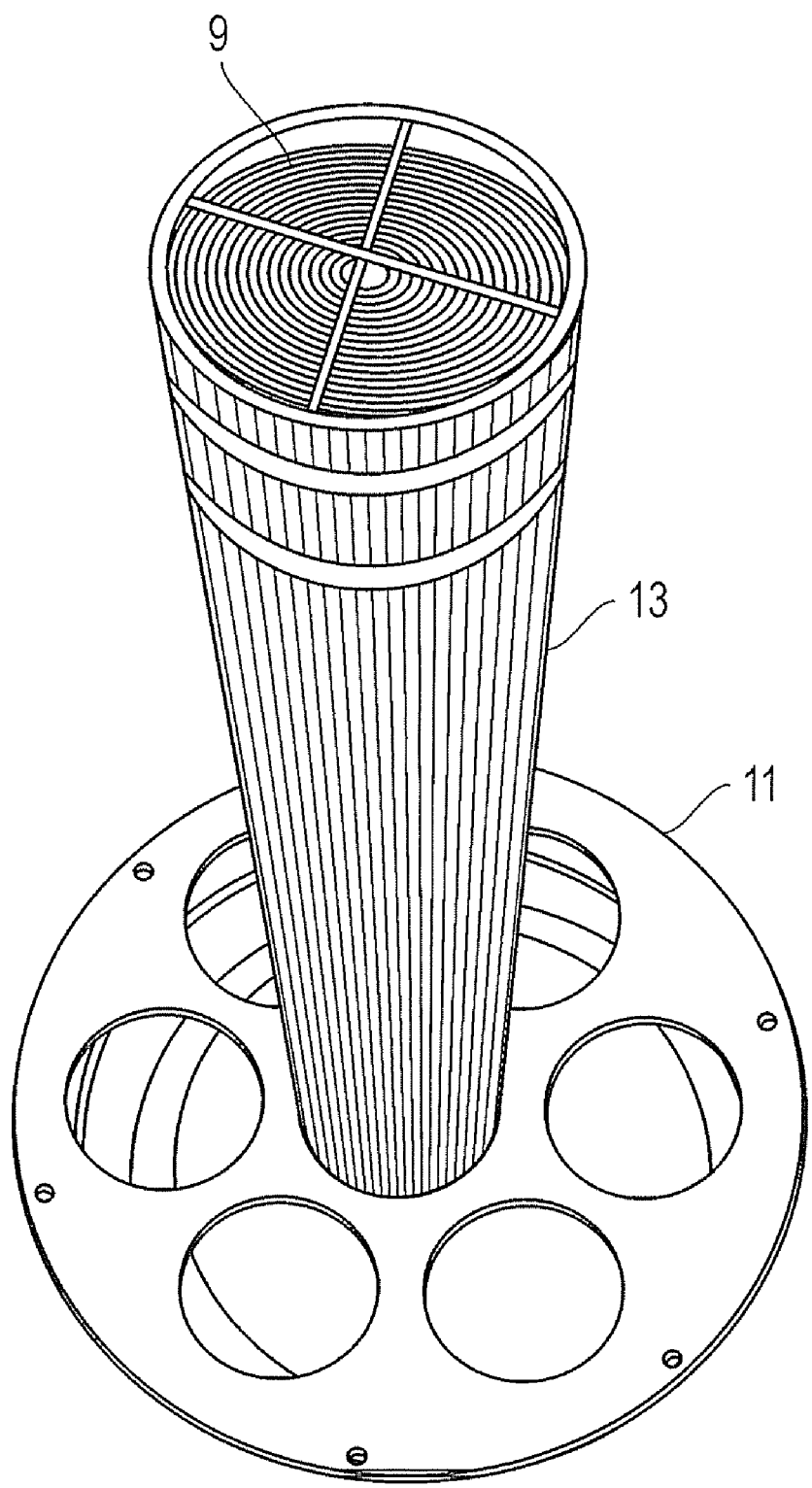
FIG. 5 shows a perspective view of one fibrous blanket cylinder installed in the guide.

FIG. 5 shows a fibrous blanket cylinder 13 being positioned in the center hole of the guide 11. In one configuration, the fibrous blanket cylinder 13 is made by wrapping the fibrous blanket in a punched metal web and/or metal mesh and overlapping the ends. Although the word cylinder is used in the nomenclature of the fibrous blanket cylinders 13, they may be configured as an oval, square, triangular or any other shape in which a tube may be formed. The fibrous blanket used to construct the fibrous blanket cylinder 13 may be made of any material capable of filtering particulate materials, including one or more of an aramid, a meta-aramid, a polyamide, a polyphenylene sulfide, a p-phenylene-1,3,4-oxadiazole, polytetrafluoroethylene, and basalt. A cap of the same or similar material may be placed over the distal end of the fibrous blanket cylinders 13. In addition, a bobbin 9 may be affixed at the distal end of one or more of the fibrous blanket cylinders 13.

Figure 6:
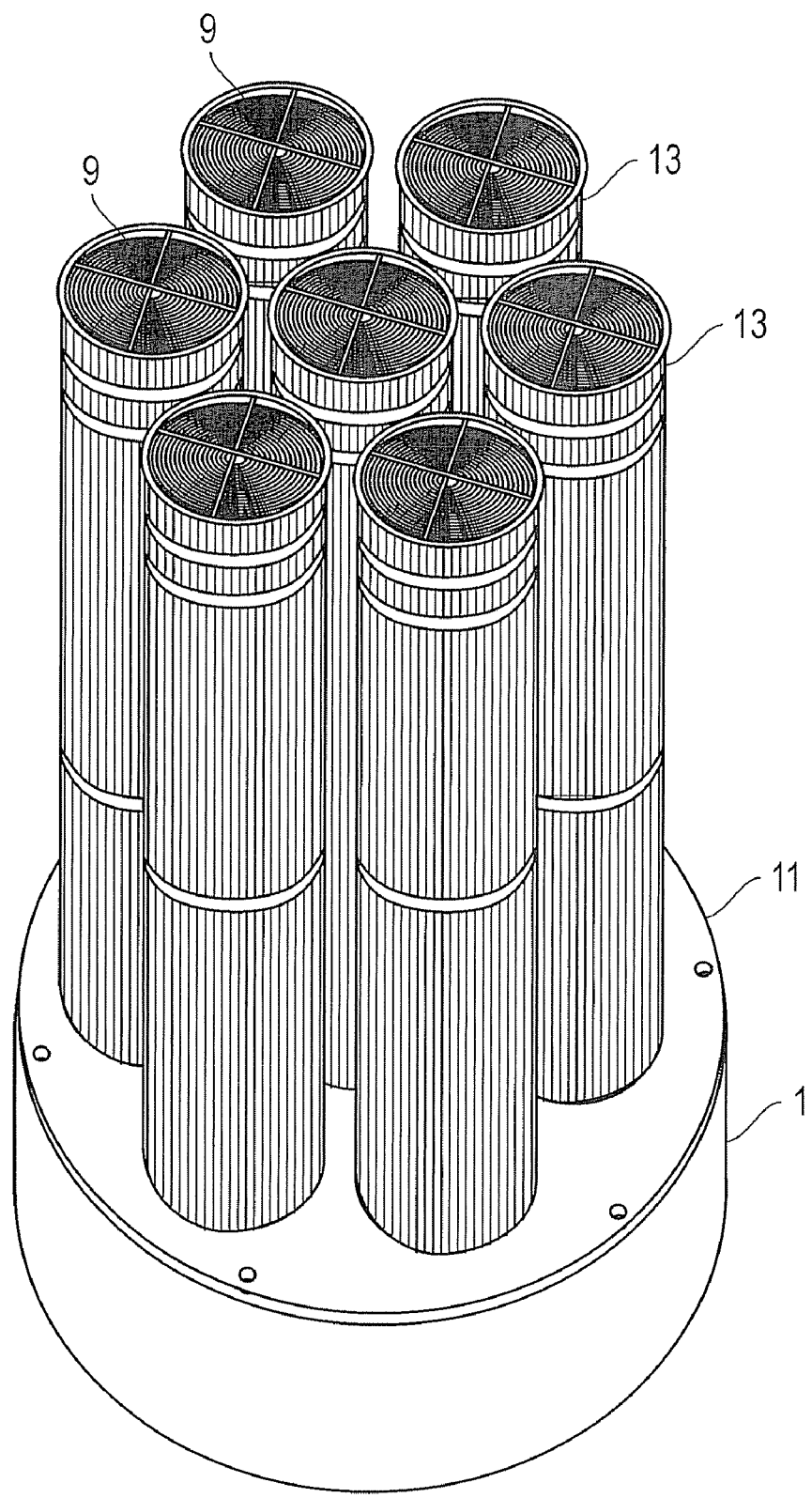
FIG. 6 shows a perspective view of six fibrous blanket cylinders installed in the guide.
Figure 7:
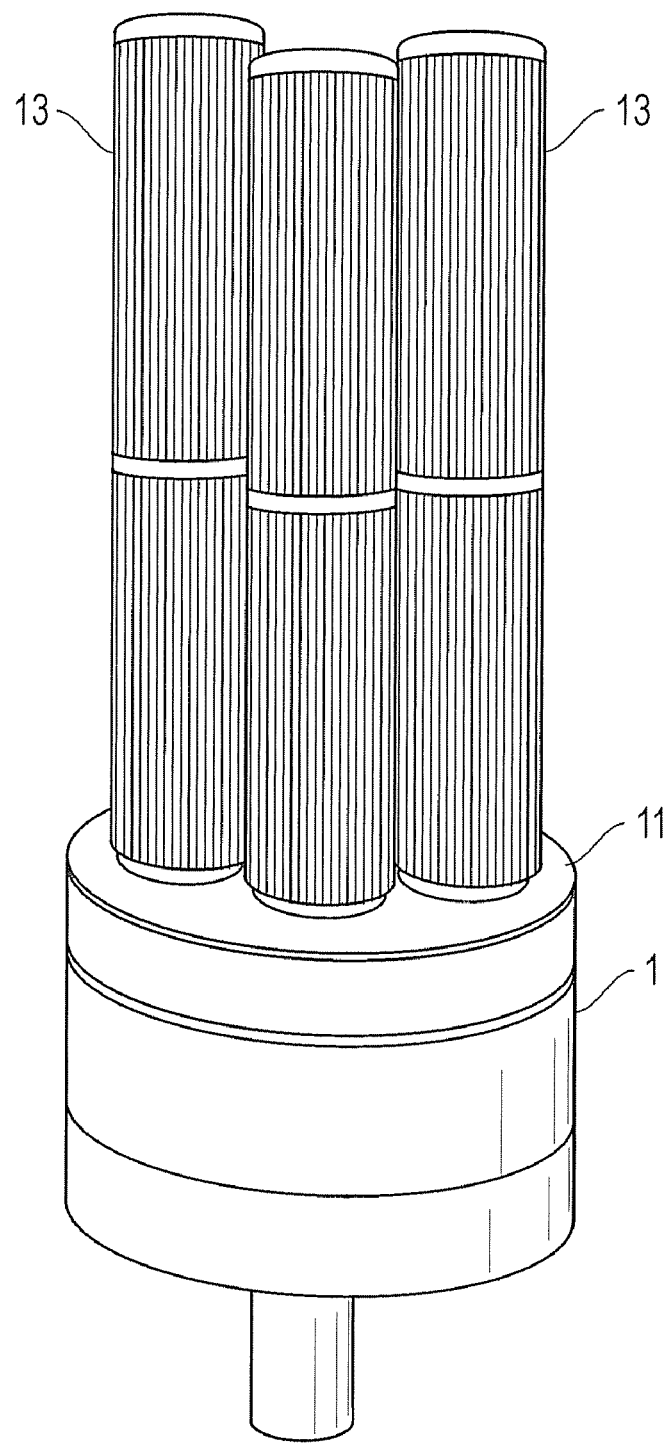
FIG. 7 shows a side view of the fibrous blanket cylinders installed in the guide.

FIG. 6 shows a perspective view of seven fibrous blanket cylinders 13 configured in the guide 11 and FIG. 7 shows a side view of the fibrous blanket cylinders 13 configured in the guide 11. It is important to note that, while seven fibrous blanket cylinders 13 are depicted, the number may be increased or decreases as the application may require.

Figure 8:
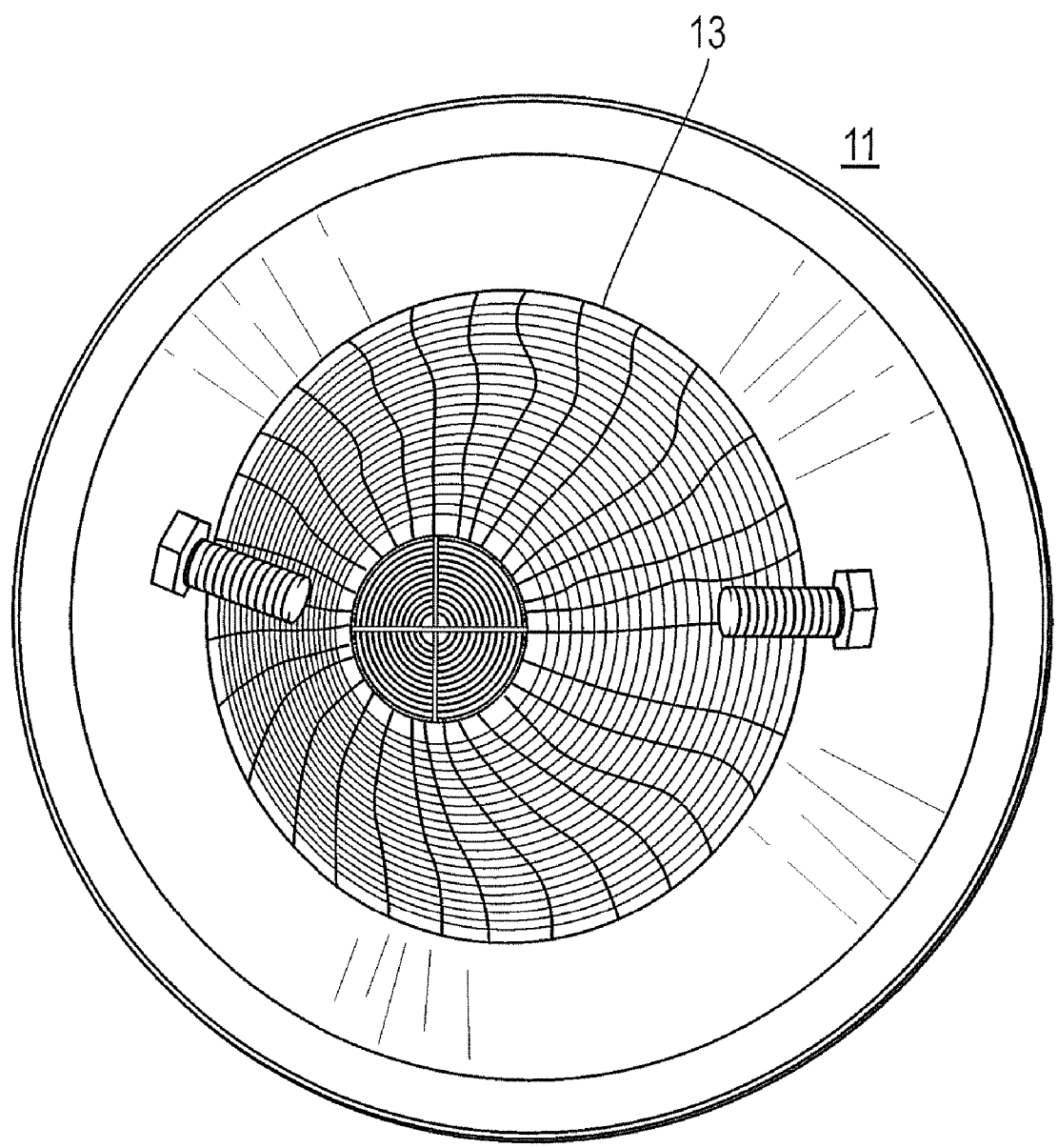
FIG. 8 shows a bottom view of one of the fibrous blanket cylinders.
Figure 9:
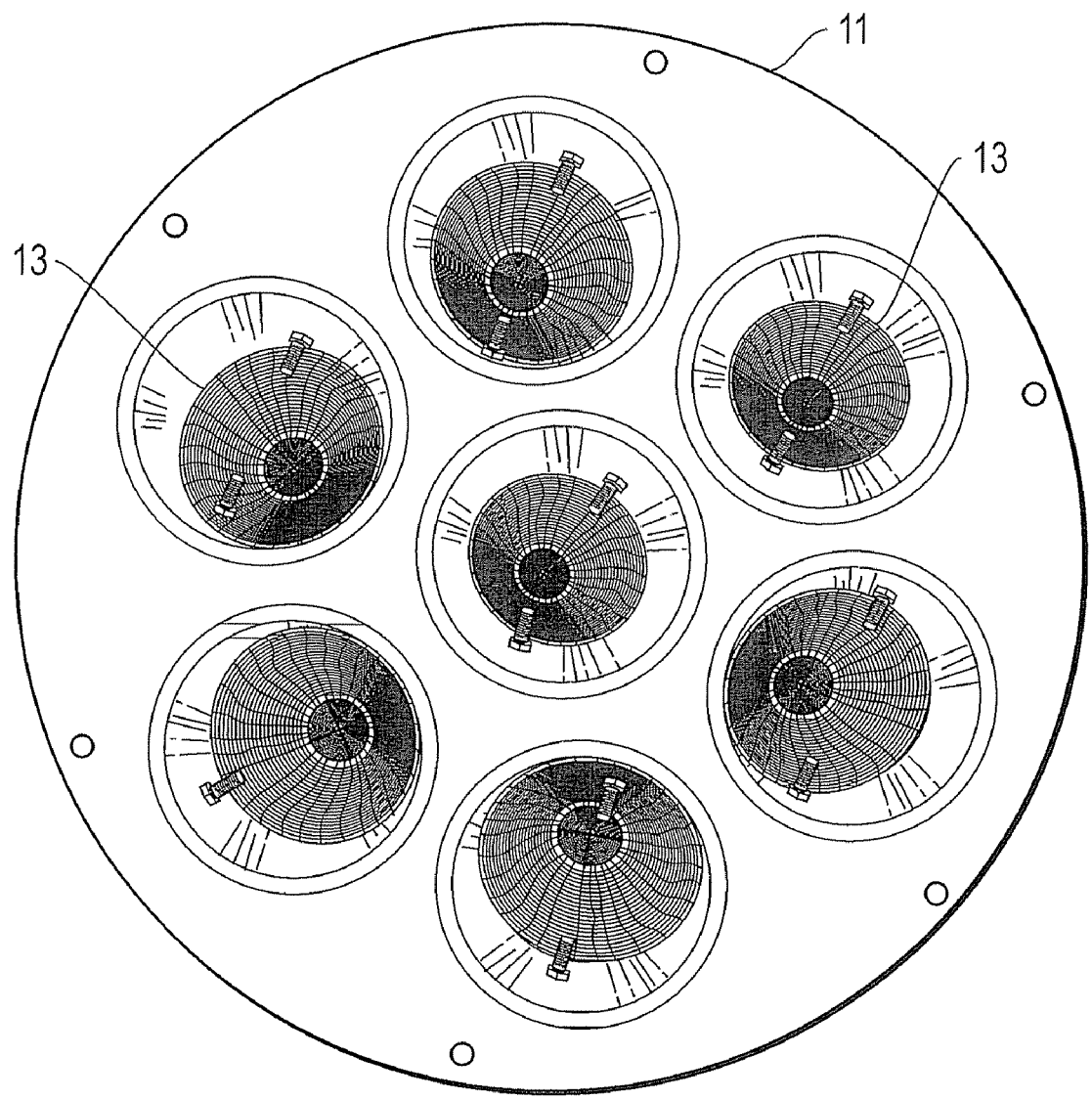
FIG. 9 shows a bottom view of the fibrous blanket cylinders affixed in the guide.

FIG. 8 shows a bottom view of one of the fibrous blanket cylinders 13 and FIG. 9 shows a bottom view of the fibrous blanket cylinders 13 affixed in the guide 11.

Figure 10:
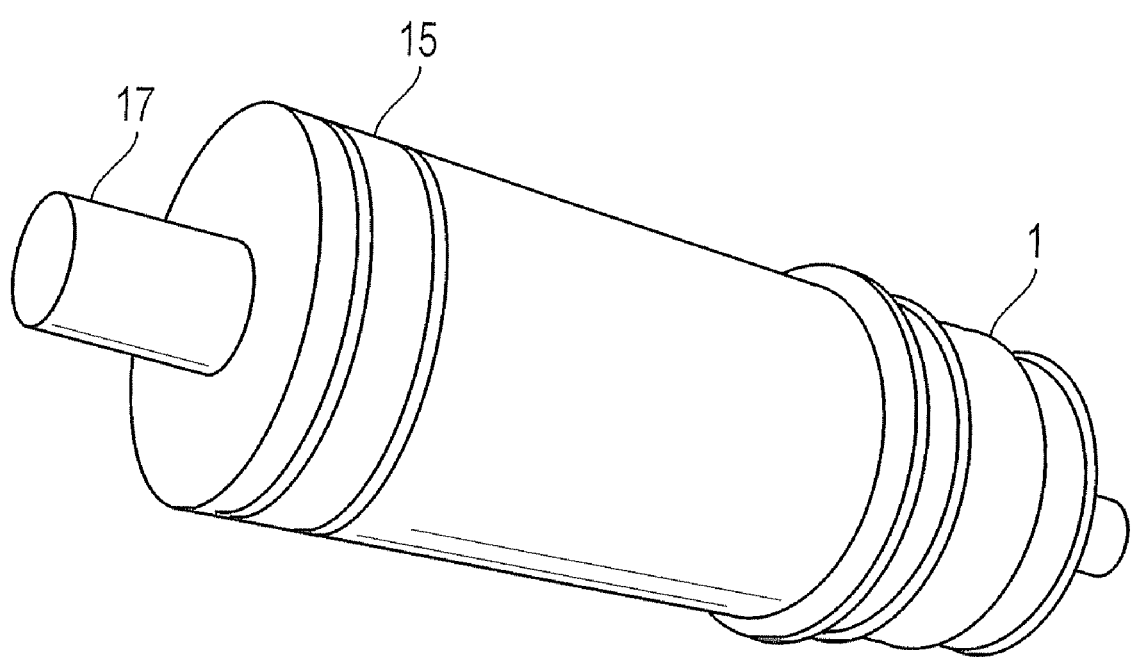
FIG. 10 shows one embodiment of the device of the present invention with the upper portion of the outer casing attached.

FIG. 10 shows one embodiment of the device of the present invention with the upper portion of the outer casing 15 attached. The upper portion of the outer casing 15 is configured with an exhaust outlet 17 may be made of any material capable of withstanding the heat and pressure of the application, such as for example, steel, aluminum, aluminized steel or stainless steel. The upper portion of the outer casing 15 may be attached to the lower portion of the outer casing 1 in a variety of ways using a variety of attachment devices known in the art including by securing the upper casing to the lower casing by placing fasteners through holes 2 (shown in FIG. 1) in the lower portion aligned with holes in the upper portion. The upper portion of the outer casing 15 may be either permanently or removably attached to the lower portion of the outer casing 1.

When the device of the resent invention is installed on the exhaust system of a diesel engine, gas leaves the exhaust pipe and enters the exhaust inlet 3. The gas flows through the bobbin 9 or, in an alternative embodiment, flows first through the diaphragm and then through the bobbin 9. In either case, a portion of the gas is allowed to escape through the side of the carcass 5 due to the bevel 7. Some portion of the gas proceeds through the bobbin 9 and out the distal end of the carcass 5 through the perforations or screen. The gas then proceeds through the fibrous blanket cylinders 13 and out the exhaust outlet 17.

Both the bobbin 9 and the fibrous blanket cylinders 13 act as material particle filters. In the bobbin 9, the gathering of material particles is accomplished by the collection of particles in the walls of the bobbin 9. The particles agglutinate as a result of the lost of speed and due to their own physical characterstics. The fibrous blanket cylinders 13 collect material particles that do not pass through the material. These two systems of gathering of material particles are efficient and can be cleaned and reused.

The bobbin 9 may be constructed using different metals, such as aluminum, zinc, copper, iron and others, to generate an electric or voltage differential that makes ions available to the system.

Another important effect is the reduction of the sound emitted from the device resulting from the dampening of the shockwaves of gases against the bobbin 9 and the fibrous blanket cylinders 13

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of possible filters, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

What is claimed is:

1. A device for reducing emissions comprising:
    an outer casing with an exhaust inlet and an exhaust outlet;
    a carcass affixed to the exhaust inlet with a bobbin positioned at the distal end of said carcass; and
    one or more fibrous blanket cylinders positioned inside said outer casing.

2. The device of claim 1 wherein said bobbin is constructed by wrapping two fabrics of different metal around a central point.

3. A device for reducing emissions comprising:
    an outer casing with an exhaust inlet and an exhaust outlet;
    a carcass affixed to the exhaust inlet with one or more fibrous blanket cylinders positioned inside said outer casing and wherein a bobbin is positioned at the distal end of one or more of said fibrous blanket cylinders.

4. A method for reducing emissions comprising:
    affixing the proximal end of an outer casing to the exhaust outlet of a diesel engine wherein said outer casing has an exhaust inlet and an exhaust outlet;
    affixing a carcass to said exhaust inlet, wherein said carcass has a bobbin positioned at the distal end of said carcass; and
    positioning one or more fibrous blanket cylinders inside said outer casing.

5. The method of claim 4 wherein said bobbin is constructed by wrapping two fabrics of different metal around a central point.

* * * * *

UNITED STATES PATENT AND TRADEMARK OFFICE
CERTIFICATE OF CORRECTION

| | | |
|---|---|---|
| PATENT NO. | : 7,731,773 B2 | Page 1 of 1 |
| APPLICATION NO. | : 11/743911 | |
| DATED | : June 8, 2010 | |
| INVENTOR(S) | : Sangiovani | |

It is certified that error appears in the above-identified patent and that said Letters Patent is hereby corrected as shown below:

Column 4,

Line 61, "400 horsepower" should read --1,400 horsepower--.

Signed and Sealed this
Fifth Day of April, 2011

David J. Kappos
*Director of the United States Patent and Trademark Office*